(12) United States Patent
Blank et al.

(10) Patent No.: US 8,100,879 B2
(45) Date of Patent: Jan. 24, 2012

(54) CONNECTOR DEVICE FOR ENTERAL ADMINISTRATION SET

(75) Inventors: Ricardo Blank, Mies (CH); Jean Daniel Ginzburg, Viry (FR); Jörg Heinzerling, Bad Herzfeld (DE)

(73) Assignee: Nestec S.A., Vevey (CH)

( * ) Notice: Subject to any disclaimer, the term of this patent is extended or adjusted under 35 U.S.C. 154(b) by 729 days.

(21) Appl. No.: 10/701,698

(22) Filed: Nov. 5, 2003

(65) Prior Publication Data

US 2004/0153047 A1 Aug. 5, 2004

(30) Foreign Application Priority Data

| Nov. 18, 2002 | (GB) | 0226730.0 |
| Dec. 19, 2002 | (GB) | 0229624.2 |
| Feb. 13, 2003 | (GB) | 0303317.2 |
| May 19, 2003 | (GB) | 0311463.4 |

(51) Int. Cl.
| A61M 5/32 | (2006.01) |
| A61B 19/00 | (2006.01) |
| B67D 1/00 | (2006.01) |
| B65D 47/00 | (2006.01) |
| B67D 3/00 | (2006.01) |
| B32B 27/10 | (2006.01) |
| B65D 77/00 | (2006.01) |
| B65D 69/00 | (2006.01) |
| B65D 71/00 | (2006.01) |

(52) U.S. Cl. ........ 604/411; 604/403; 604/404; 604/414; 604/415; 222/81; 222/82; 222/87; 222/88; 222/544; 428/34.2; 206/216; 206/550

(58) Field of Classification Search .......... 604/411–415, 604/540, 541, 317, 323, 324, 326, 327, 328, 604/332, 355, 19, 21, 48, 93.01, 244, 246, 604/257, 262, 277, 523, 533–535, 537; 206/438; 222/80, 81, 155, 159, 541.1–541.9; 184/85
See application file for complete search history.

(56) References Cited

U.S. PATENT DOCUMENTS

| 1,528,283 | A | * | 3/1925 | Whitesides | 222/90 |
| 2,668,533 | A | * | 2/1954 | Evans | 604/405 |
| 2,969,063 | A | * | 1/1961 | Broman | 604/246 |
| 3,001,525 | A | * | 9/1961 | Hendricks | 604/416 |
| 3,542,240 | A | | 11/1970 | Solowey | |
| 3,599,836 | A | * | 8/1971 | Hegi | 222/90 |
| 3,973,698 | A | * | 8/1976 | Kato | 222/91 |

(Continued)

FOREIGN PATENT DOCUMENTS

CA 2 432 623 A1 * 6/2002

(Continued)

OTHER PUBLICATIONS

Vaughan et al., "Bacterial Safety of a Closed Administration System for Enteral Nutrition Solutions", Journal of American Dietetic Association, vol. 88, pp. 35, (1988).

(Continued)

*Primary Examiner* — Leslie Deak
*Assistant Examiner* — Adam Marcetich
(74) *Attorney, Agent, or Firm* — K&L Gates LLP (57) ABSTRACT

The present invention relates to a connector device suitable for connecting an enteral administration set to a laminated paper packaging system comprising enterally administrable medical or nutritional food.

20 Claims, 9 Drawing Sheets

U.S. PATENT DOCUMENTS

| | | | |
|---|---|---|---|
| 4,022,258 A | | 5/1977 | Steidley |
| 4,189,072 A | * | 2/1980 | Conn .......................... 222/519 |
| 4,296,786 A | | 10/1981 | Brignola |
| 4,475,670 A | * | 10/1984 | Rutter .......................... 222/83 |
| 4,544,336 A | * | 10/1985 | Faeser et al. ................. 417/412 |
| 4,560,382 A | | 12/1985 | Isono |
| 4,801,007 A | * | 1/1989 | Rule .......................... 206/217 |
| 4,826,500 A | | 5/1989 | Rautsola |
| 4,881,662 A | * | 11/1989 | Tallman ........................ 222/81 |
| 4,888,008 A | | 12/1989 | D'Alo et al. |
| 4,895,275 A | | 1/1990 | Quinn et al. |
| 4,921,138 A | * | 5/1990 | Quinn et al. .................... 222/85 |
| 4,997,429 A | | 3/1991 | Dickerhoff et al. |
| 5,052,614 A | * | 10/1991 | Xuan .......................... 229/103.1 |
| 5,125,886 A | * | 6/1992 | Dirksing ...................... 493/87 |
| 5,228,592 A | * | 7/1993 | Pellerano ...................... 222/83 |
| 5,303,751 A | | 4/1994 | Slater et al. |
| 5,531,681 A | * | 7/1996 | Walton et al. ................. 604/83 |
| 5,851,608 A | * | 12/1998 | Yamada et al. ............. 428/34.2 |
| 5,960,992 A | | 10/1999 | Bernstein et al. |
| 5,971,207 A | * | 10/1999 | McDonough et al. ............ 222/1 |
| 5,993,422 A | * | 11/1999 | Schafer .......................... 604/154 |
| 6,139,534 A | | 10/2000 | Niedospial, Jr. et al. |
| 6,223,924 B1 | | 5/2001 | Ek et al. |
| 6,336,912 B1 | * | 1/2002 | Bourguignon .................. 604/65 |
| 6,378,730 B1 | * | 4/2002 | Reddy et al. ................... 222/83 |
| 6,382,462 B1 | | 5/2002 | Ostergaard-Nielsen et al. |
| 6,422,412 B1 | | 7/2002 | Sagawa |
| 6,485,479 B1 | | 11/2002 | Knierbein |
| 6,551,639 B1 | * | 4/2003 | Nye et al. ...................... 426/117 |
| 6,621,700 B1 | | 9/2003 | Roman et al. |
| 6,651,845 B1 | * | 11/2003 | Schroeder ...................... 222/83 |
| 6,742,678 B1 | * | 6/2004 | Krystopik, Jr. ............. 222/481.5 |
| 6,932,239 B2 | * | 8/2005 | McKitrick ...................... 222/83 |
| 7,232,044 B1 | * | 6/2007 | Salmela .......................... 222/83 |
| 2003/0226855 A1 | * | 12/2003 | Allanson et al. ................ 222/83 |
| 2004/0104246 A1 | * | 6/2004 | Kawaguchi et al. ............. 222/83 |

FOREIGN PATENT DOCUMENTS

| | | | |
|---|---|---|---|
| DE | | 3627231 | 8/1986 |
| DE | | 39 06 418 A1 * | 9/1990 |
| EP | | 0 376 629 A2 * | 12/1989 |
| EP | | 0 367 629 | 10/1992 |
| EP | | 0 711 538 | 10/1997 |
| EP | | 0 947 433 | 10/1999 |
| EP | | 1 088 765 | 4/2001 |
| EP | | 1 262 412 | 12/2002 |
| EP | | 1 352 843 | 10/2003 |
| GB | | 2 105 695 | 7/1982 |
| WO | | 8806025 | 8/1988 |
| WO | | 9316595 | 9/1993 |
| WO | | WO 93/20772 | 10/1993 |
| WO | | 9832428 | 7/1998 |
| WO | | WO 98/41452 | 9/1998 |

OTHER PUBLICATIONS

"Entralife Closed System", Corpak, Inc., Wheeling, IL (1989).
Entera-Flo Spike, Fresenius Pharma USA, Inc, New Brunswick, NJ.
Compat-Universal set, Sandoz Nutrition.
Tubulures pour pompas à nutrition, Fresenius Vial (a company of Fresenius HemoCare).
United Kingdom Search Report.
Abstract of EP 0 355 795 from EPO Aug. 9, 2005. Machine translation of EP 0 355 795 from babelfish.altavista.com.
Abstract of EP 1 129 682 from EPO Aug. 9, 2005. Machine translation of EP 1 129 682 from babelfish.altavista.com.
Abstract of FR 2 802 430 from EPO Aug. 9, 2005. Machine translation of FR 2 802 430 from babelfish.altavista.com.
McCarty, M F: "Nitric oxide deficiency, leukocyte activation, and resultant ischemia are crucial to the pathogenis of diabetic retinopathy/neuropathy: Preventive potential of antioxidants, essential fatty acids, chromium, ginkgolides, and pentoxylline" May 1998, Medical Hypothesis, vol. 50, nr. 5, pp. 435-559 (XP008031833).
Nazif, Naglaa M: "Phytoconstituents of Zizyphus spina-christi L. fruits and their antimicrobial activity" Jan. 2002, Food Chemistry, vol. 76, No. 1, pp. 77-81 (XP002285033).
Broca, C et al.: "4-Hydroxyisoleucine Experimental Evidence of Its Insulinotropic and Antidiabetic Properties" Oct. 1999, American Journal of Physiology, vol. 277, No. 4, pp. E617-E623 (X0000909894).

* cited by examiner

CONNECTOR DEVICE FOR ENTERAL ADMINISTRATION SET

The present invention relates to a connector device for an enteral administration set and a laminated paper packaging system according to the features of the independent claim to a prefabricated enteral administration comprising such connector device, to a kit comprising such connector device, an enteral administration set and a laminated paper packaging system, and to a kit comprising such prefabricated enteral administration system and a laminated paper packaging system.

Such connector device, e.g. a sterile connector device, helps in establishing a connection between the feeding line of an enteral, e.g. nutritional, administration set and a laminated paper packaging system, such as Tetra Brik®, containing medical or nutritional fluids or compositions which are to be enterally administered to a patient, by allowing the flow of a composition contained in the laminated paper packaging system to the enteral administration set through the connector device.

Many individuals in hospitals or nursing homes cannot orally take nourishment or medication. These individuals, or medical patients, typically receive medical flowable materials, e.g. fluids, containing the required nourishment and/or medication enterally via a patient feeding line of an enteral administration set that is connected to a packaging system containing such medical or nutritional flowable materials. These medical or nutritional flowable materials are commonly packaged in flexible packaging systems, for example flexible pouches. For economical and other reasons, such pouches are disadvantageous.

Millions of laminated paper packaging systems, such as Tetra Brik®, are used in the food industry. They provide a convenient cost-effective and lightweight paperboard container, for every type of pourable, e.g. liquid, product. They exist in a myriad of sizes, from 0.2 liter to 1.5 liter, or even larger. Because they are opaque, they are perfect for light-sensitive enterally administrable compositions, for example compositions containing vitamins. With regard to medical fluids that are to be administered to a patient, these fluids typically need to be sterile. Laminated paper packaging systems may be sterilized, and therefore may keep even the most perishable liquid foods fresh and nutritious for months, without refrigeration or added preservatives. Finally, the laminated paper packaging systems may be aseptically and air tightly closed, preventing contaminants and/or oxygen from entering the container. Such laminated paper packaging systems may be advantageously used to contain pharmaceutical or nutritional compositions, e.g. enteral medical or nutritional fluids.

However, the existing enteral administration sets are not adapted to being connected, e.g. directly connected, to the existing laminated paper packaging systems. Consequently, medical or nutritional compositions, e.g. fluids, have to be poured into an intermediate container which is then connected to the feeding line of an enteral administration set. This is inconvenient for patients and medical personnel: Moreover sterility is difficult to ensure.

Therefore, it is an object of the invention to provide a connector device that is convenient to handle and that can be directly connected to both existing laminated paper packaging systems as well as to existing enteral administration sets.

According to the invention, a connector device for an enteral administration set and a laminated paper packaging system is suggested. The connector device comprises: means adapted to fit to the enteral administration set, means adapted to fit to the laminated paper packaging system, and a passageway adapted to allow the flow of a composition contained in the laminated paper packaging system from the laminated paper packaging system to the enteral administration set through the connector device. Such a connector device allows direct attachment of the connector to both the enteral administration set as well as to the laminated paper packaging system in a convenient manner. Such direct connections to the laminated paper packaging system and/or the enteral administration set may be oxygen-tight and/or sterile.

In one embodiment of the connector device according to the instant invention, the means adapted to fit to the enteral administration set comprise a rigid tube part for attachment of the feeding line of the enteral administration set. The tube part contains a part of the passageway for the composition to be administered. The typically flexible feeding line of the enteral administration set can be attached to the connector device by frictionally fitting the flexible feeding line onto the rigid tube part of the connector device, thus establishing a passageway between the connector device and the enteral administration set. Alternatively or in addition, glue can be used to establish a secure and tight fit of the feeding line on the tube part. The means adapted to fit to the laminated paper packaging system comprise an internally threaded portion adapted to be screwed onto a corresponding outwardly threaded portion of a frame-like member of the laminated paper packaging system. That is to say, attachment of the connector to the laminated paper packaging system is achieved by a threaded connection of the type of a cap that is threaded onto the neck of a container. In order now to establish a passageway between the interior of the laminated paper packaging system and the connector device, the connector device further comprises means for opening of the laminated paper packaging system upon screwing the connector onto the frame-like member of the laminated paper packaging system. That is to say, once the connector device is screwed onto the frame-like member of the laminated paper packaging system, the laminated paper packaging system is opened, thus establishing a passageway between the interior of the laminated paper packaging system and the connector device. On the other hand, as described above, the passageway between the connector device and the enteral administration set is established by fitting the feeding line of the enteral administration set on the tube part of the connector device. Thus, a complete passageway between the interior of the laminated paper packaging system and the enteral administration set is established allowing the flow of the composition contained in, the laminated paper packaging system through the connector device to the enteral administration set.

In a more specific embodiment of the connector device according to the invention, the means for opening of the laminated paper packaging system comprise a cutting member protruding from the connector device in a direction towards the laminated paper packaging system. The cutting member is intended to cut the laminated paper packaging system upon screwing the connector onto the frame-like member of the laminated paper packaging system, thus opening the laminated paper packaging system. This type of opening means is a direct opening means, since cutting of the laminated paper packaging system is performed by the cutting member itself.

In another more specific embodiment of the connector device according to the invention, the means for opening of the laminated paper packaging system comprise a triggering member protruding from the connector device in a direction towards the laminated paper packaging system for acting upon a leverage system being provided in the frame-like member of the laminated paper packaging system, the leverage system breaking the laminated paper packaging system when being acted upon by the triggering member. This type of opening means is an indirect opening means, since the triggering member itself does not open the laminated paper packaging system, but rather actuates upon a the leverage system, that breaks the laminated paper packaging system. Accordingly, this type of opening means requires the presence of a leverage system in the frame-like member of the laminated paper packaging system.

In another embodiment of the connector device according to the invention, the means adapted to fit to the enteral administration set comprises a rigid tube part for attachment of the feeding line of the enteral administration set. The tube part contains a part of the passageway for the composition to be administered. The typically flexible feeding line of the enteral administration set can be attached to the connector device by frictionally filling the flexible feeding line onto the rigid tube part of the connector device, thus establishing a passageway between the connector device and the enteral administration set. Alternatively or in addition, glue can be used to establish a secure and tight fit of the feeding line on the tube part. So far, the attachment of the feeding line of the enteral administration set is similar to the one already described above. However, in contrast to the embodiment described above, the means adapted to fit to the laminated paper packaging system comprise a spike for penetrating into the interior of the laminated paper packaging system as well as an attachment means for fixedly attaching the connector device to the laminated paper packaging system. The attachment means for attaching the connector device to the laminated paper packaging system can be embodied in different ways, examples will be explained in detail further below. The spike further comprises a continuation of that part of the passageway, that is contained in the tube part, into the interior of the laminated paper packaging system, thus establishing the complete passageway from the interior of the laminated paper packaging system to the enteral administration set.

As already mentioned above, the attachment means for fixedly attaching the connector device to the laminated paper packaging system can be embodied in different ways. In one embodiment, the attachment means comprise a rim having an upper surface facing towards the laminated paper packaging system. An adhesive layer is provided on the upper surface for attaching the connector device to the laminated paper packaging system upon penetration of the spike and pressing of the upper surface of the rim with the adhesive layer against the laminated paper packaging system. The only action for the person using the connector is to have the spike penetrate the laminated paper packaging system and to press the rim with the adhesive on its upper surface against the laminated paper packaging system in order to glue the connector device to the laminated paper packaging system. For convenience of storage, the adhesive layer can be protected by a protecting cover, e.g. a foil, that must be peeled off prior to installing the connector device.

In another embodiment, the attachment means for fixedly attaching the connector device to the laminated paper packaging system comprise two rims extending in parallel around the spike axially spaced from each other at a predetermined distance. That rim which is located nearer to the point of the spike is made from a flexible material, whereas that rim which is located farther from the point of the spike is made from a rigid material. The flexibility of the rim located nearer to the spike facilitates insertion of the rim after a hole has been formed in the laminated paper packaging system with the aid of the point of the spike. The rim located farther from the point of the spike remains outside the laminated paper packaging systems and abuts against the outer wall of the laminated paper packaging system. The two rims are axially spaced from one another at a distance so as to achieve a safe fit of the connector device, that is to say the wall of the laminated paper packaging system is fixedly enclosed between the two axially spaced rims. While the connector can be manufactured by injection molding, the flexible rim can be manufactured for example by co-molding a suitable flexible material such as rubber or a flexible polyolefin.

All of the embodiments of the connector devices described above do not necessarily comprise, but advantageously comprise a venting means in order to allow the laminated paper packaging to remain its shape upon emptying it from the composition to be administered. Such a venting means may, for example, comprise a valve means allowing air to enter through the valve means while preventing the composition to be administered to exit and/or to flow through the venting means.

In a further embodiment of the connector device according to the invention, the connector device further comprises a visualization tube. One end of the visualization tube is connected to the passageway for the composition to be administered while the other end of the visualization tube is connected to a venting means. The venting means itself comprises an air inlet as well as a spike that is arranged to penetrate into the interior of the laminated paper packaging system at a predetermined level. During emptying of the laminated paper packaging system, air is able to enter into the laminated paper packaging system through the vented spike penetrating into the interior of the laminated paper packaging system at the predetermined level, thus providing for equilibration of pressure. As a consequence, the level of the fluid contained in the visualization tube and the level of fluid contained in the laminated paper packaging system is even, thus allowing the user to see the level of fluid contained in the laminated paper packaging system although the laminated paper packaging system itself may be opaque.

A further aspect of the instant invention deals with a prefabricated enteral administration system comprising an enteral administration set and a connector device non-releasably connected to the enteral administration set, wherein the connector device is a connector device as described above. Such a prefabricated enteral administration system need only be attached to the laminated paper packaging system, there is no need to assemble the administration set and the connector. Such a prefabricated system further reduces the risk of contamination, in particular when it is used as a single-use (i.e. disposable) system, that is disposed of after use and is not sterilized and reused again.

In one embodiment of the prefabricated enteral administration system according to the invention, the system may comprise a pump unit arranged in the feeding line of the enteral administration set for feeding the fluid from the laminated paper packaging system.

In a further embodiment of the enteral administration set according to the invention, the system comprises a transparent intermediate bag for accommodating the volume of composition contained in the laminated paper packaging system. In essence, such system is intended for gravity feeding, firstly allowing to empty the content of fluid contained in the laminated paper packaging system into the transparent intermediate bag in order to enable the user to always see the remaining quantity of fluid. The fact, that the intermediate bag is a part of the prefabricated system assures the high level of safety against contamination, while at the same time allowing to see the remaining quantity of fluid.

A further embodiment of the prefabricated enteral administration system according to the invention comprises a dosing means for controlling the speed of administration of composition to the patient. This embodiment allows to control the speed of administration, regardless of the speed of the pump feeding or the gravity feeding.

A further aspect of the invention deals with an enteral administration kit comprising an enteral administration set, a connector device as described above and a laminated paper packaging system containing a composition to be enterally administered to a patient. Such a kit is advantageous inasmuch as the patient has a complete system that must only be assembled in order to be ready to be used and does not need to control the inventory of each of the parts of the system.

A further aspect of the invention deals with an enteral administration kit comprising a prefabricated enteral administration system as described above, and a laminated paper packaging system containing a composition to be enterally administered to a patient. Such a kit of parts has the same advantages as described in the preceding paragraph, however, assembly is simplified and the risk of contamination is further reduced.

The enteral administration kits as hereinabove described may be aseptically assembled, i.e. may constitute closed, e.g. aseptic closed systems. As used herein, the term "aseptic" means free of microorganisms, e.g. substantially free of microorganisms, e.g. when in use.

Further advantageous embodiments become apparent from the following description of embodiment of the invention with the aid of the drawings, in which.

When used herein, the term "compositions" is intended to encompass nutritional and medical compositions, e.g. nutritional and medical flowable materials, in particular fluids, and in particular enteral compositions. According to the invention, these compositions are contained in a laminated paper packaging system. Also, the term "fluids" is used to refer to such compositions.

The term "laminated paper packaging system" may refer to, for example, laminated paper packaging systems of the type Tetra Brik®, Tetra Brik Aseptic®, Tetra Pak®, Tetra® Prisma, Tetra Recart®, Tetra Square®, Tetra Top®, Elopak®, Combiblok®, Pure Pak®. Laminated paper packaging system may be from about 0.125 liter to about 2 liters volume, preferably from about 0.200 liter to about 1 liter volume. Most preferred sizes include about 0.200, about 0.250 and about 1 liter.

Such laminated paper packaging systems may comprise layers of fibrous material, such as paper or cardboard, which are coated on either side with a thermoplastic material such as polyethylene. On that side of the laminated paper packaging material which is destined to be in contact with the composition, there may be also a layer of barrier material, such as e.g. aluminum foil, which may also be coated with a thermoplastic layer. Such laminated paper packaging systems are disclosed for example in U.S. Pat. No. 6,223,924 or EP1088765, which are hereby incorporated by reference. Techniques to sterilize such laminated paper packaging systems are known to one skilled in the art. Packaging machines have been developed to aseptically fill and seal such laminated paper packaging systems, e.g. sterilized laminated paper packaging systems, with sterilized food products or compositions.

The connector device according to the invention permits the connection between an enteral administration set, e.g. the feeding line of an enteral administration set, and a laminated paper packaging system. The device permits the flow of a composition contained in the laminated paper packaging system from the laminated paper packaging system into the enteral administration set through the connector device, when the connector device is connected, e.g. sealably connected, thereto. As used herein, the term "sealably connected" refers to a connection which temporally or permanently prevents leakage of the composition when the composition is flowing through the connector device, so that a liquid-tight connection is formed. The connection between the connector device of the invention and the laminated paper packaging system and/or an enteral set may also be air-tight, e.g. oxygen-tight, and/or sterile.

As used herein, the term "enteral administration set" encompasses all components starting with the feeding line located between the connector device as hereinabove described, and the patient, for example the tube feeding line. As will be described further below, optionally a plastic bag sealably connected to the tube feeding line may be provided in the enteral administration set. Such a plastic bag may be substantially collapsible. It may further be substantially transparent, e.g. transparent. It may also be vented or contain air, e.g. sterilized air.

Such a plastic bag may be reversibly or permanently connected to the connector device. The permanent connection of the connector device to the plastic bag may for example be made by methods including, but not limited to, heat induction, ultrasonic welding and friction welding or any other methods as known in the art. The plastic bag, may be connected directly or indirectly, e.g. through a feeding tube, to the connector device. Such a plastic bag may have a capacity of about 100 ml to about 1 liter, e.g. of 200 ml to about 500 ml, e.g. of about 250 ml.

The composition may be fed by gravity, and the set may be equipped with a roller clamp for controlling the flow rate (rate of administration). Alternatively or in addition, the enteral administration set may include a pump, e.g. of the type Compat® from Novartis Nutrition Corporation (Minneapolis, Minn.). These details will be outlined further below.

Figure 1:
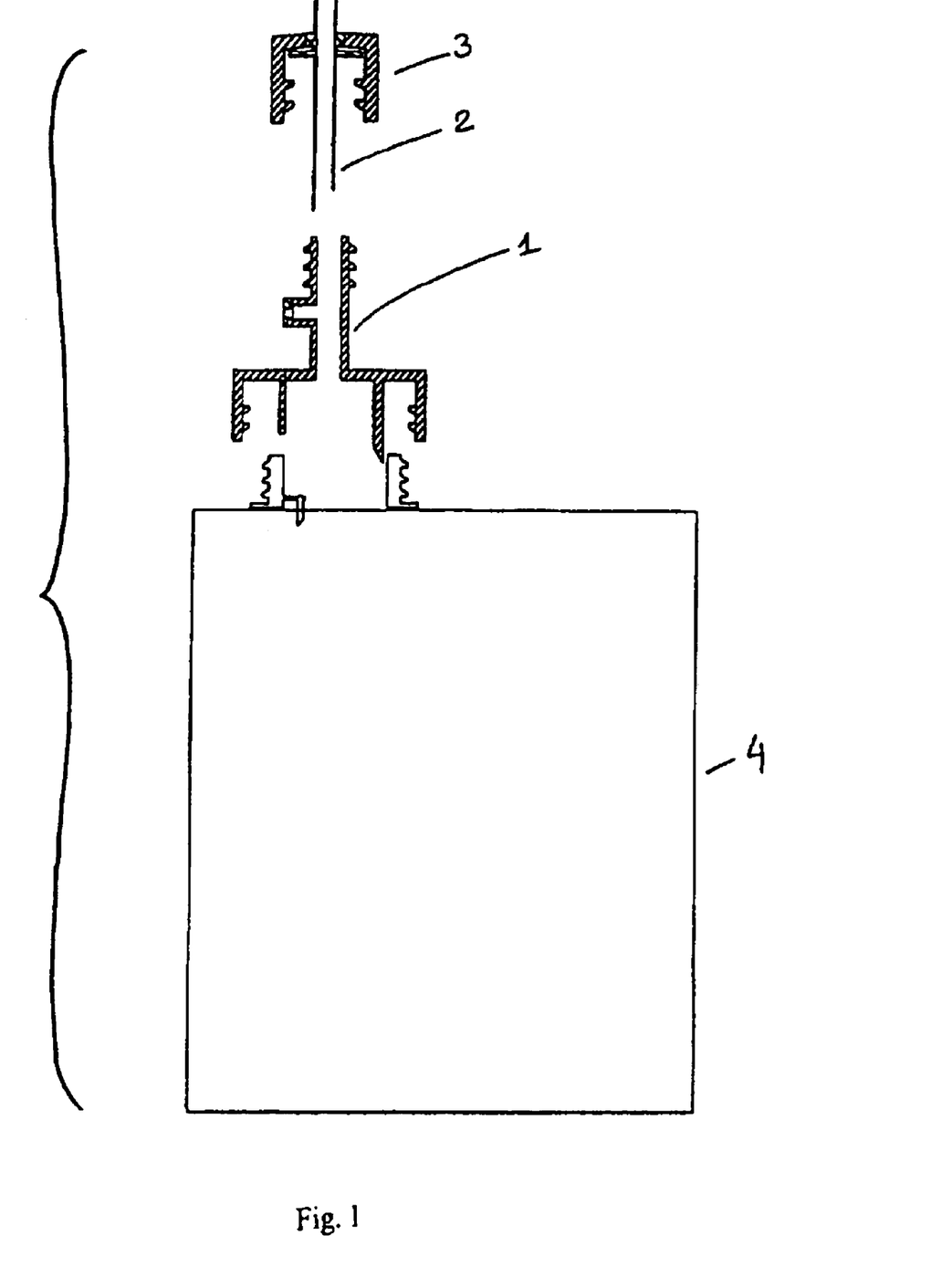
FIG. 1 shows an exploded cross-sectional view of an embodiment of a connector device according to the invention, connected to a feeding line of an enteral administration set and a laminated paper packaging system.
Figure 2:
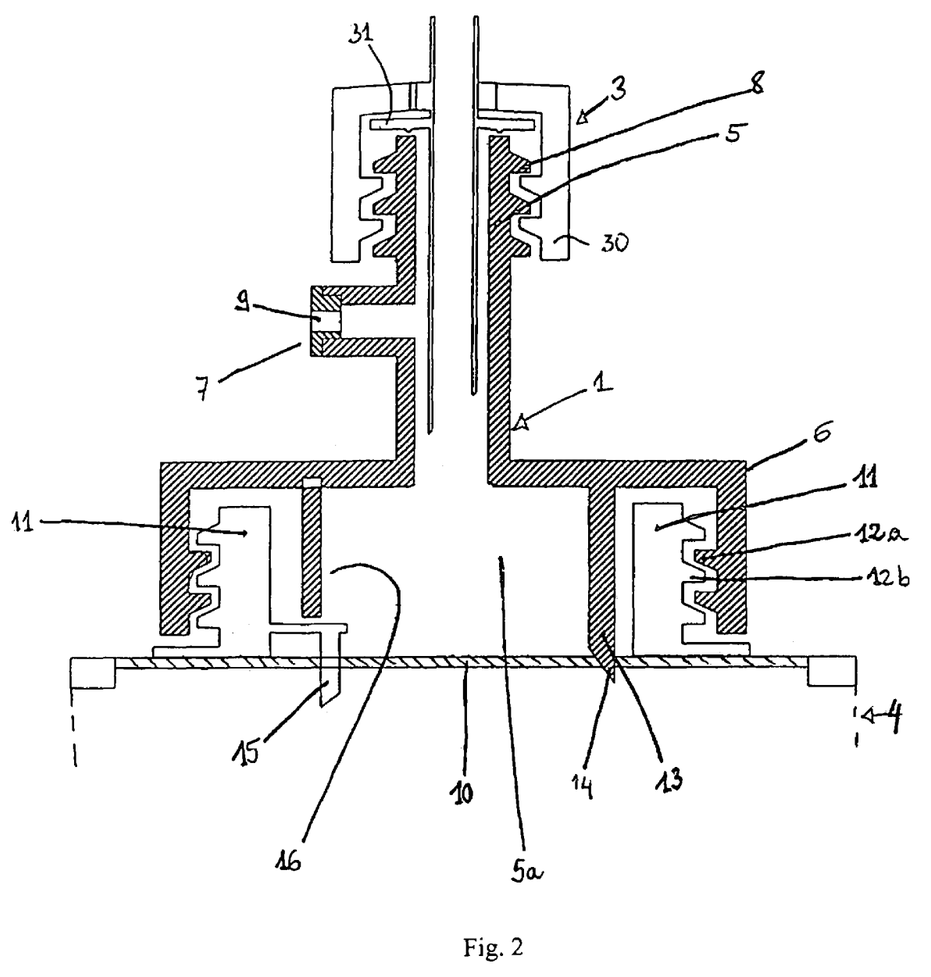
FIG. 2 shows an enlarged cross-sectional view of the connector device shown in FIG. 1.

Referring now to the drawings and in particular to FIG. 1 and FIG. 2, connector device 1 may be sealably connected to an enteral administration set 3, e.g. to the feeding line 2 of enteral administration set 3, and to a laminated paper packaging system 4. Connector device 1 may comprise an outwardly threaded section 5 adapted to engage a corresponding internally threaded section 30 of enteral administration set 3. By screwing section 30 of enteral administration set 3 onto section 5 of connector 1, sealing flange 31 of feeding line 2 of enteral administration set 3 sealingly engages the end face of section 5 of connector device 1, thus providing a sealed connection between enteral administration set 3, or feeding line 2 respectively, and connector device 1.

On the opposite end of connector device 1, internally threaded portion 6 having internal threads 12a may be provided. Internally threaded portion 6 is adapted to be screwed onto a corresponding outwardly threaded portion of a frame-like member 11 having corresponding threads 12b, so as to connect connector device 1 to laminated paper packaging system 4.

Internally threaded portion 6 of connector device 1 may have a diameter, e.g. internal diameter between about 1.0 cm and about 3.5 cm, preferably between about 1.3 cm and about 3.0 cm, more preferably between about 1.5 cm and about 2.5 cm, and even more preferably between about 1.8 cm and about 2.3 cm. The most preferred diameter, e.g. internal diameter of the portion 6 of connector device 1 is about 2 cm, e.g. 2.1 or 2.2 cm.

In the embodiment shown in FIG. 2, laminated paper packaging system 4 is sealed by a cover layer 10. In order to allow a composition, e.g. a fluid, contained in laminated paper packaging system 4 to be administered, cover layer 10 must be opened in order to establish a passageway from the interior of laminated paper packaging system 4 through connector device 1 into feeding line 2 of enteral administration set 3. Therefore, the embodiment shown in FIG. 2 suggests means for opening laminated paper packaging system 4 upon screwing connector device 1 onto frame-like member 11.

Frame-like member 11 is integrated within laminated paper packaging system 4, preferably affixed thereto, circumscribing cover layer 10. The frame-like member 11 of laminated paper packaging system 4 may be of the type associated with Spin® cap or Stream® cap, available e.g. from Tetra Pak Switzerland AG. Such frame-like members are known to one skilled in the art, and are described e.g. in EP0947433, EP1088765, EP1262412, U.S. Pat. No. 6,382,462, U.S. Pat. No. 6,422,412 or U.S. Pat. No. 6,223,924, which are hereby incorporated by reference. Frame-like member 11 may be integrated within laminated paper packaging system 4 by techniques known to one skilled in the art, e.g. by application of hot melt adhesive, microflame welding or laser welding. Frame-like member 11 may be closed by a second barrier layer, e.g. a foil, e.g. an aluminum foil, e.g. a pull tab, removable therefrom. In another embodiment of the invention, frame-like member 11 may be closed by a standard cap, e.g. a reclosable cap, such as a screw or push cap. In this case, access to the cover layer 10 covering the opening of laminated paper packaging system 4 may be made after removing the cap from frame-like member 11.

The opening means may comprise a cutting member 13 e.g. protruding from connector device 1 in a direction towards laminated paper packaging system 4, in particular towards cover 10. Upon connecting connector device 1 to laminated paper packaging system 4, e.g. by pressing connector device 1 thereto and/or by screwing connector device 1 onto frame-like member 11, cutting member 13 cuts laminated paper packaging system 4 thus establishing a passageway for the fluid from the interior of laminated paper packaging system 4 through connector device 1 into feeding line 2 of enteral administration set 3.

Cutting member 13 may comprise one or more cutting means, e.g. spikes 14, cutting teeth, cutter or any other suitable structure known to one skilled in the art, e.g. of the type associated with Spin® cap or Stream® cap, available e.g. from Tetra Pak Switzerland AG and as described e.g. in EP0947433, EP1088765, EP1262412, U.S. Pat. No. 6,382,462, U.S. Pat. No. 6,422,412 or U.S. Pat. No. 6,223,924, incorporated herein by reference.

The length, position and number of cutting means 13, e.g. projecting means, may be adapted to cut laminated paper packaging system 4 when connector device 1 is connected, e.g. sealably connected, thereto, e.g. screwed onto frame-like member 11. Alternatively cutting means 13, e.g. projecting means, may extend beyond the bottom of portion 6 of connector device 1.

According to the invention, opening means, e.g. cutting member 13, may be offset from the center, e.g. center axis, of connector device 1.

In another embodiment of the invention, opening means, e.g. cutting member 13, may be placed in the center of connector device 1. For example, opening means, e.g. cutting member 13, may be in prolongation from, e.g. an extension of, portion 5 of connector device 1 which is adapted to be connected to the feeding line.

According to the invention, opening means, e.g. cutting member 13, may be hollow, e.g. may include a fluid passageway.

In another embodiment of the invention, opening means, e.g. cutting member 13, may consist of a tubular member, e.g. reverse thread, provided inside connector device 1 and adapted to be engaged with frame-like member 11, e.g. by comprising external threads capable of connecting internal threads present in frame-like member 11, and to move in direction of laminated paper packaging system 4 when connector device 1 is connected, e.g. sealably connected, thereto. Such a tubular member may comprise, e.g. on its lowermost edge, at least one cutting means adapted to break laminated paper packaging system 4, upon engagement of tubular member with frame-like member 11 (not shown). Such opening means is known to one skilled in the art, e.g. associated with Stream® cap or Spin® cap, available e.g. from Tetra Pak Switzerland AG, e.g. as described in EP0947433, EP1088765 or EP1262412, which are hereby incorporated by reference.

As an alternative, FIG. 2 shows another embodiment for the means for opening laminated paper packaging system 4 upon connecting connector device 1 to the laminated paper packaging system 4, e.g. by pressing connector device 1 thereto and/or by screwing connector 1 onto frame-like member 11. According to this further embodiment, a triggering member 16 protruding from connector device 1 in a direction towards laminated paper packaging system 4, in particular towards cover 10, is provided. Frame-like member 11 of laminated paper packaging system 4 may be provided with an opening system 15, e.g. a leverage system, associated with, e.g. incorporated into frame-like member 11. Upon connecting connector device 1 to laminated paper packaging system 4, e.g. by pressing connector device 1 thereto and/or by screwing connector 1 onto frame-like member 11, triggering member 16 acts upon leverage system 15 and presses leverage system 15 towards cover 10, thus causing cover 10 to break. In this manner, a passageway for the fluid from the interior of laminated paper packaging system 4 through connector device 1 into feeding line 2 of enteral administration set 3 is established.

Opening system 15 may be movable, e.g. from a first position where it does not open laminated paper packaging system 4, e.g. where it is not into contact with it, to a second position where it opens laminated paper packaging system 4, e.g. where it protrudes below frame-like member 11. Preferably opening system 15 may be formed integrally with an elastic hinge, which may be formed integrally with frame-like member 11 (not shown).

Triggering member 16 may be arranged to be recessed, that is to say it does not protrude beyond connector 1 in order to ensure that it triggers the opening, e.g. breaking, of laminated paper packaging system 4 only when connector device 1 is fully screwed onto frame-like member 11 of laminated paper packaging system 4.

Triggering members 16 and the corresponding systems for opening the laminated paper packaging system 4 are known to one skilled in the art. For example, the triggering member 16 of connector device 1 is of the type of the actuation system associated with Spin® cap or Stream® cap, e.g. as described in EP0947433, EP1088765, EP1262412, U.S. Pat. No. 6,223, 924, U.S. Pat. No. 6,422,412 or U.S. Pat. No. 6,382,462, incorporated herein by reference.

A venting means 7 may be provided for allowing air to enter the interior of laminated paper packaging system 4 in order to compensate for the fluid exiting laminated paper packaging system 4. The venting means may comprise a valve system allowing air to enter through the valve means while preventing the composition to be administered to exit through the valve. A filter 9, e.g. a bacterial filter, may be provided in order to allow filtration of the air and to prevent contaminants such as bacteria from entering feeding line 2 and or connector device 1 and/or laminated paper packaging system 4.

It will be appreciated that such venting means may alternatively be positioned in the feeding line 2 of enteral administration set 3, or in laminated paper packaging system 4. Preferably, such venting means are positioned in connector device 1, even more preferably in portion 6 of connector device 1 which is connected to laminated paper packaging system 4. In addition, visualization means for visualizing the level of fluid may be provided (not shown here, detailed explanation to follow further below).

According to the invention, after being opened, laminated paper packaging system 4 may be prevented from interfering with the flow of the composition contained therein, for example by using opening means, e.g. a single cutter movable in spiral, as described in EP1088765, which is hereby incorporated by reference, or by any other suitable means known in the art.

The tightness of connection between connector device 1 and laminated paper packaging system 4 may be ensured by means known in the art, e.g. by adhesive, glue, gasket, by foam or elastomere, by direct top contact, or by so-called "olive tightness type", e.g. such as that present in the thread caps of bottles containing carbonated beverages. It will be appreciated that one skilled in the art is fully enabled to select a suitable tightness system.

Figure 3:
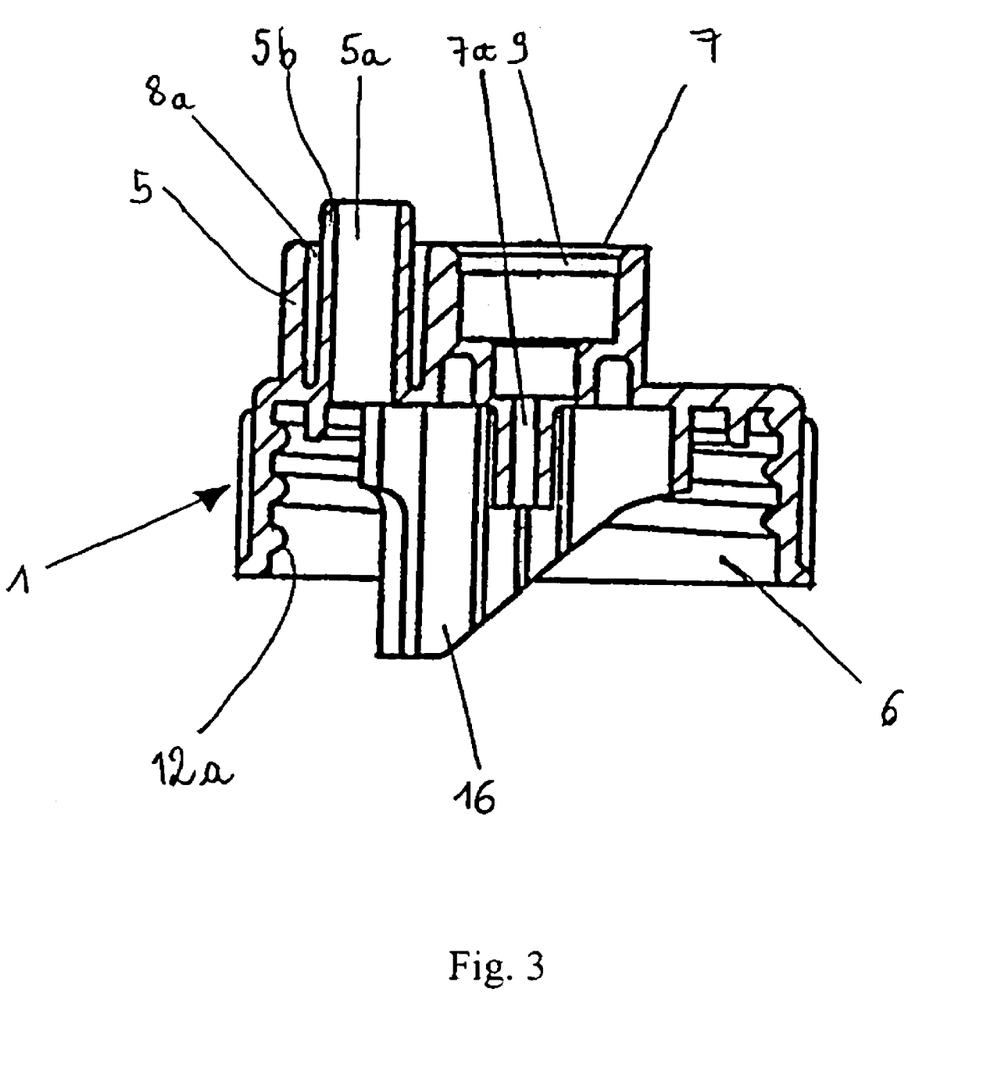
FIG. 3 shows a cross-sectional view of a further embodiment of a connector device according to the invention, which is adapted to indirectly open a laminated paper packaging system upon being connected thereto.

FIG. 3 shows an embodiment of a connector device 1 according to the invention. As explained with reference to FIG. 1 and FIG. 2, connector device 1 of FIG. 3 can be screwed with the aid of an internally threaded portion that is screwed onto a corresponding outwardly threaded portion of a frame-like member 11 of laminated paper packaging system 4 (not shown in FIG. 3). Triggering member 16 may act upon leverage system 15 provided in frame-like member 11 of the laminated paper packaging system, as this has been explained in detail above. Feeding line 2 of enteral administration system 3 (not shown in FIG. 3) can be sealingly attached to a rigid tube part 5b of section 5 of connector device 1 by frictional engagement, that is to say by moving feeding line 2 of enteral administration set 3 into ring-like slot 8a so as to achieve a tight fit, e.g. by a snap-fit. A circumferential tab section projecting from portion 5 of connector device 1 which is adapted for connecting to feeding line may engage a rim at the end of feeding line, sealably connecting connector device 1 to feeding line (not shown in FIG. 3). After engagement, connector device 1 may be further adhered to feeding line 2 by sealing, e.g. sonic or ultrasonic welding, friction welding, heat induction, or by using adhesive, e.g. hot melt adhesive, or glue, or by any other method as known in the art.

The venting means 7 may be arranged such that the air passageway 7a allows air, e.g. air filtered by filter 9, to penetrate into laminated paper packaging system (not shown) without penetrating into the fluid passageway 5a, as this is shown in FIG. 3. The passage of composition from the laminated paper packaging system through air passageway 7a may be prevented by a flexile membrane forming filter 9 which is positioned adjacent to the inner opening of the air passageway, as this is described for example in U.S. Pat. No. 4,997,429, which is incorporated herein by reference. Such venting means are known and commercially available in existing enteral administration sets, e.g. of the type Compat® from Novartis Nutrition Corporation (Minneapolis, Minn.). Venting means 7 may be arranged such that air passageway 7a substantially is arranged in the center of connector device 1.

Feeding line 2 of enteral administration set 3 may comprise a portion with an enlarged diameter, e.g. a diameter larger than the diameter of the rest of the feeding line, e.g. a drip chamber, in order to allow fluid to be seen flowing from laminated paper packaging system 4. Such an enlarged portion of feeding line 2, e.g. drip chamber, may be substantially transparent. It may be positioned near connector device 1 or may be that portion of feeding line 2 which is directly connected, e.g. interlocked or linked, to the connector device (not shown).

Figure 4:
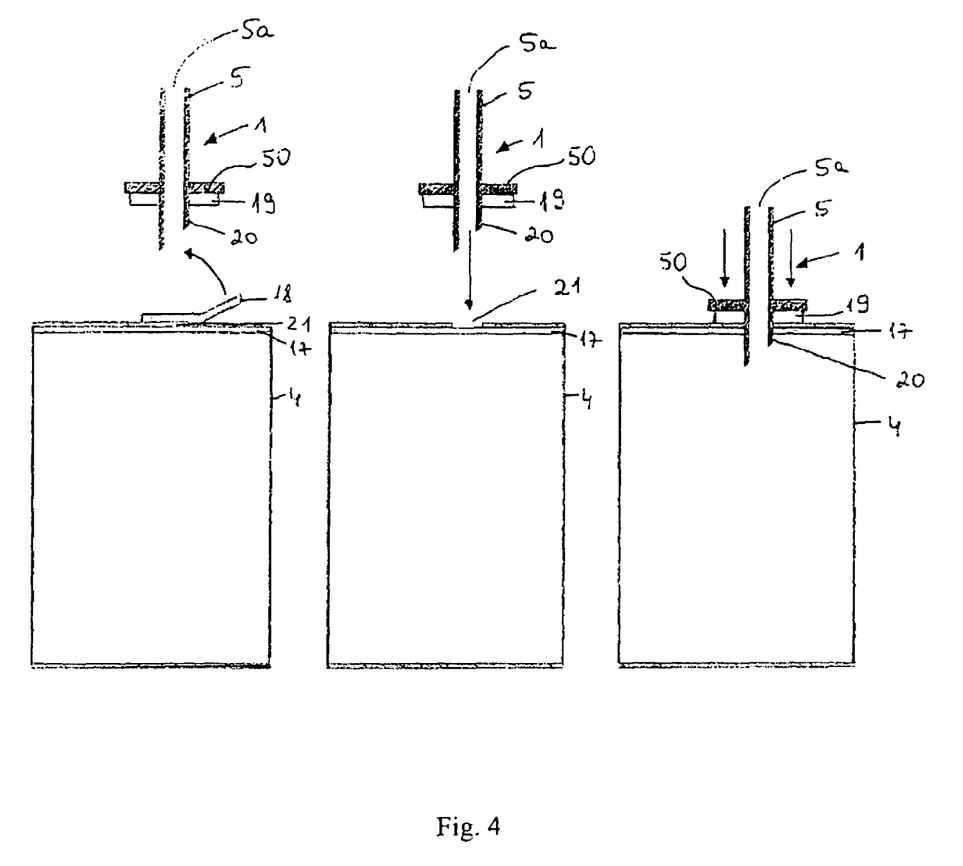
FIG. 4 shows a cross-sectional view of the steps for connecting an embodiment of the connector device according to the invention to a laminated paper packaging system.

Turning now to FIG. 4, the essential steps for connecting a specific embodiment of connector device 1 to laminated paper packaging system 4 are shown. Laminated paper packaging system 4 comprises a hole 21 in the paper board, or a thickness reduced portion, e.g. portion where a hole may be formed through some of the layers of the laminated paper packaging materials and where one or more aluminum and/or polyethylene barrier layers-extend over the hole, which may be a straw hole (i.e. a hole covered by an aluminum foil 17) or which may be a through hole (i.e. an opening). Hole 21 may be of any suitable shape or dimension, e.g. circular or rectangle, e.g. may have a diameter of about 0.3 to 3 cm, e.g. of about 0.6 to about 2 cm, e.g. of about 1.2 to about 1.5 cm, e.g. of about 1.3 to about 1.4 cm, preferably of about 0.6 cm. Hole 21 may be covered with a pull tab 18, e.g. a double pull tab, which has to be removed prior to connecting the connector device 1. For example, pull tab 18 can be peeled off.

Connector device 1 may comprise section 5 which forms a rigid tube part for attachment of the feeding line 2 of enteral administration set 3 (not shown in FIG. 4), and a spike 20 for penetrating into the interior of laminated paper packaging system 4. In case hole 21 is a straw hole, spike 20 pierces aluminum foil 17 in order to penetrate into the interior of laminated paper packaging system 4. Spike 20 according to the invention may also be able to pierce any part of laminated paper packaging system 4, e.g. a part of laminated paper packaging system 4 which does not contain a reduced thickness portion and/or a hole or a part of the laminated paper packaging system which contains a pre-cut portion. Connector device 1 comprises a rim 50 that has an upper surface (which faces downwardly in FIG. 4) facing towards laminated paper packaging system 4. An adhesive layer 19 may be provided on the upper surface of rim 50. Adhesive layer 19 can be, for example, a self-adhesive tape which may be protected by a cover foil prior to being used, or it can be a layer of adhesive or glue. Once spike 20 has penetrated into the interior of laminated paper packaging system 4, the upper surface of rim 50 provided with the adhesive layer 19 is pressed against laminated paper packaging system 4 (see arrows in FIG. 4) in order to attach, e.g. fixedly attach, connector device 1 to laminated paper packaging system 4.

Figure 5:
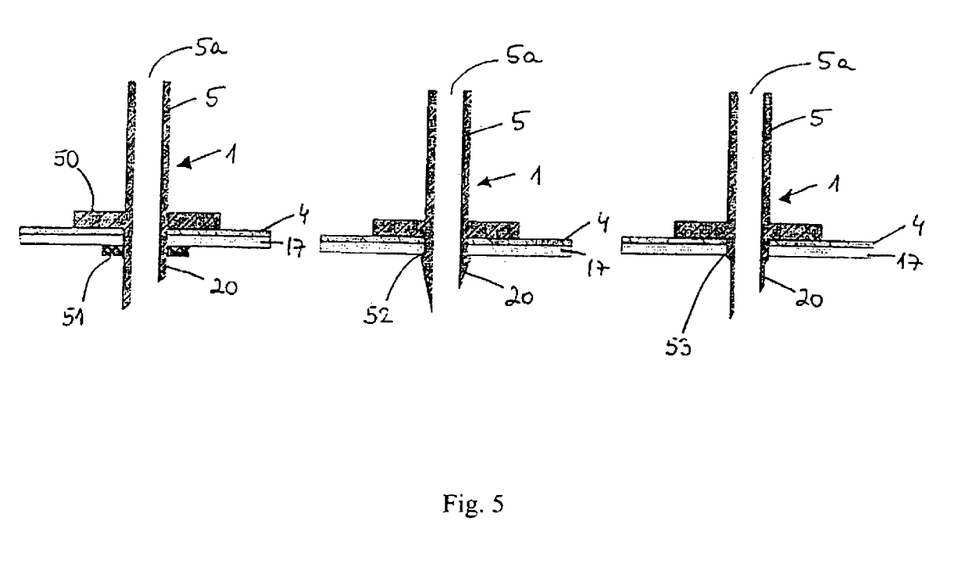
FIG. 5 shows a cross-sectional view of further embodiments of connector devices according to the invention, connected to laminated paper packaging systems.

FIG. 5 shows further embodiments of the connector device 1 according to the invention. The embodiment of connector device 1 shown on the left hand side in FIG. 5 comprises section 5, i.e. tube portion, for attachment of the feeding line of the enteral administration set. In addition, two rims 50,51 may be provided. Rims 50,51 may extend in parallel around spike 20 and may be axially spaced from each other at a predetermined distance. This predetermined distance may be chosen such that laminated paper packaging system 4 and aluminum foil 17 are fittingly arranged between rim 50 and rim 51. Rim 51, which is arranged nearer to the point of spike 20, is made from a flexible material whereas rim 50 is made from a rigid material. The flexibility of rim 51 is important in this embodiment of the invention since rim 51 must be introduced through hole 21 (see FIG. 4) into the interior of the laminated paper packaging system without damaging the laminated paper packaging system. In order to allow such introduction, rim 51 must be sufficiently flexible. Once spike 20 has been introduced into the interior of laminated paper packaging system 4 laminated paper packaging system 4 and aluminum foil 17 are fittingly compressed between rim 51 and rim 50 thus establishing a tight fit. Composition may then exit from the interior of laminated paper packaging system 4 through the thus established passageway 5a.

Connector device 1 shown on the left hand side in FIG. 5 can be manufactured by molding, and in particular flexible rim 51 can be manufactured by co-molding it together with the remainder of connector device 1 in a single step, except that the material to be used in the area of rim 51 must be a flexible material such as rubber, or a suitable flexible polyolefin, whereas the remainder of connector device 1 is molded from a rigid material, such as for example polypropylene.

The embodiment shown in the center in FIG. 5 essentially differs from that shown on the left hand side in that there is no rim 51 extending around spike 20, but that there is provided a recess 52 instead, and in that the whole connector device 1 is made from a rigid material.

With respect to the embodiment shown on the right hand side in FIG. 5, again the whole connector device 1 is made from a rigid material. The spike 20 has a thickened portion 53 in the area of hole 21 (see FIG. 4), so that the outer diameter of spike 20 is a little larger than the inner diameter of hole 21 so as to form a tight press fit.

Figure 6:
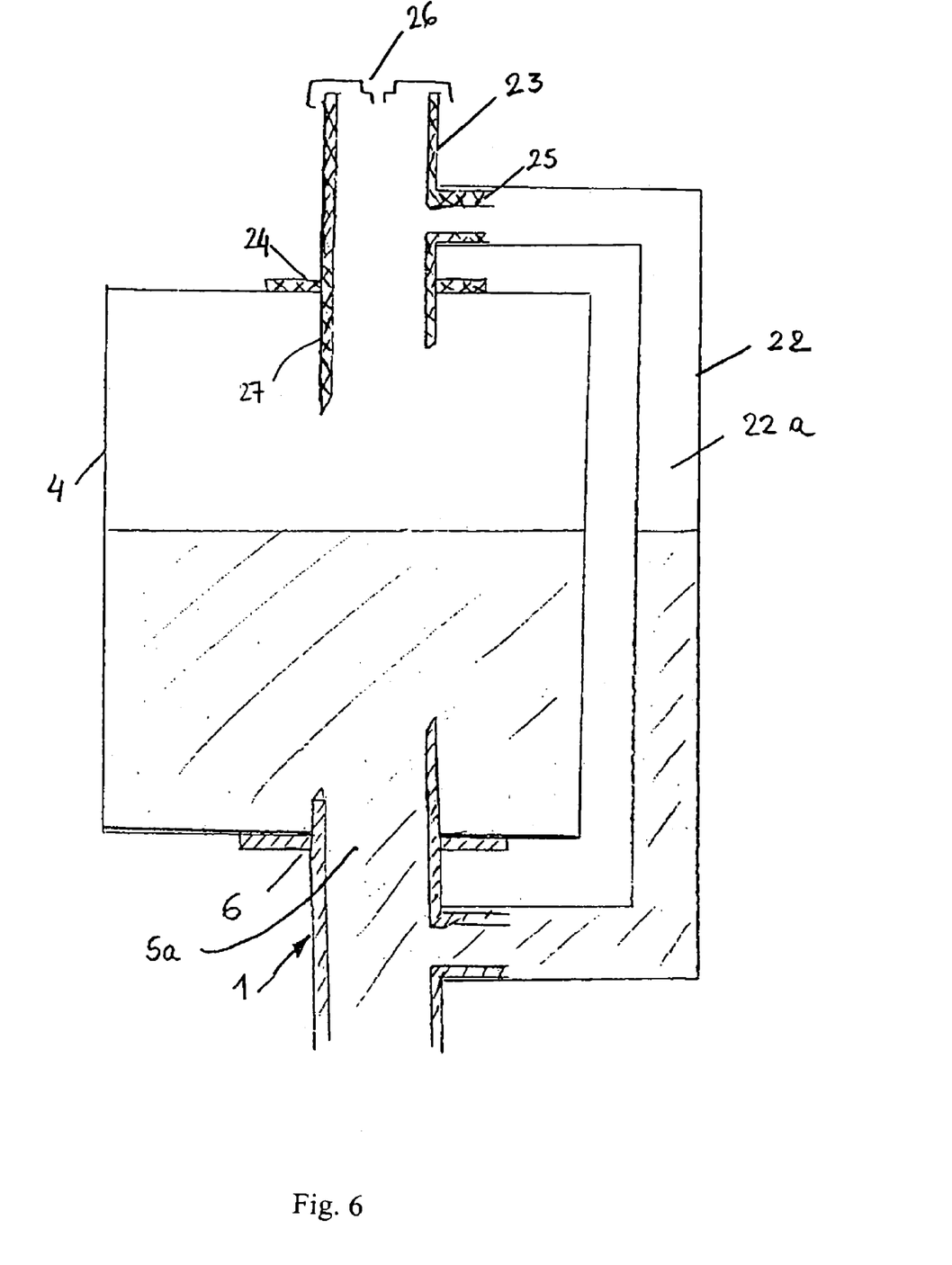
FIG. 6 shows a cross-sectional view of a further embodiment of a connector device according to the present invention, connected to a laminated paper packaging system.

FIG. 6 shows a further embodiment of connector device 1. This embodiment is provided with visualization tube 22 serving as a level indicator. One end of visualization tube 22 may be connected to passageway 5a for the composition to be administered while the other end of visualization tube may be connected to a venting means. The venting means may comprise an air inlet 26 and optionally a valve system and a filter, as well as a spike 27 that is arranged to penetrate into the interior of laminated paper packaging system 4 at a predetermined level. In the embodiment shown in FIG. 6, vented spike 27 penetrates through the top wall of laminated paper packaging system 4, however, spike 27 could also penetrate through a side wall of laminated paper packaging system 4. Visualization tube 22 is attached through section 25 to the venting means, so that there is an equilibrated pressure in the interior of laminated paper packaging system 4 and in visualization tube 22. Accordingly, the level of composition is even both in the interior of laminated paper packaging system 4 and in the visualization tube 22. Thus, visualization tube 22 serves as a level indicator.

The venting means including spike 27 can be fixedly attached to laminated paper packaging system 4 with the aid of a rim 24, that surface of rim 24 facing laminated paper packaging system 4 may be provided with glue or adhesive, or can be connected to laminated paper packaging system by any other suitable means.

Figure 7:
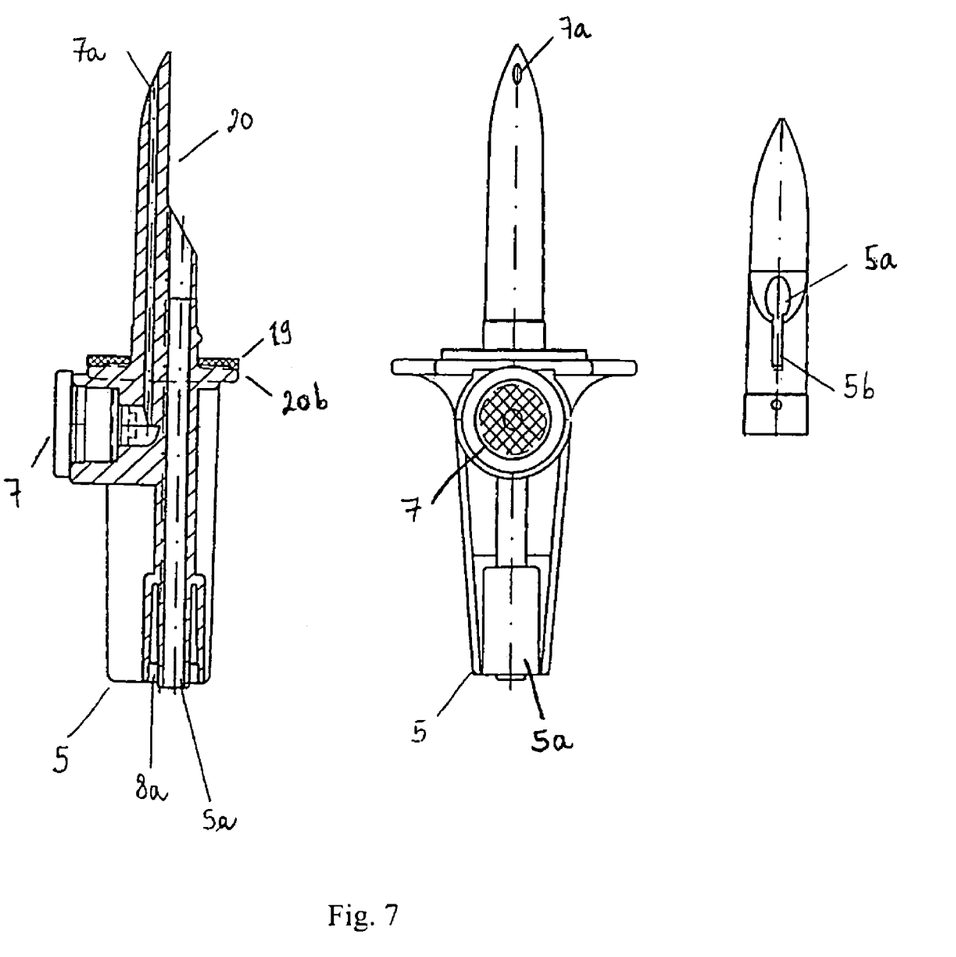
FIG. 7 shows a cross-sectional view of a further embodiment of a connector device according to the invention.

FIG. 7 shows a further embodiment of a connector device according to the invention. Connector device 1 has a rigid tube portion for attachment of the feeding line of an enteral administration set (not shown in FIG. 7), surrounded by a ring-like slot 8a. The way how to fixedly attach the feeding line of the enteral administration set to the rigid tube portion has already been described in detail with reference to the embodiment shown in FIG. 3 and need not be repeated therefore. Connector device 1 comprises a spike 20, or a cannula, e.g. a vented spike, having a rim 20b. That surface of rim 20b facing laminated paper packaging system 4 (not shown) may be provided with an adhesive layer 19, as already described in detail above. Spike 20 comprises two separate passageways, i.e. for the composition to exit from the laminated paper packaging system and passageway 7a for the air to enter the interior of laminated paper packaging system. As already discussed, a suitable filter membrane can be comprised by venting means 7 in order to prevent contaminants to enter and in order to prevent composition to exit through air passageway 7a. Passageway 5a of spike 20 may be slotted along a part of the length of spike 20 as is shown at 5b. Spike may be of any shape.

Spike 20, e.g. piercing section of spike 20, may also contain threads.

Spike 20 may have a length of about 0.5 to about 10 cm, e.g. about 0.5 to about 7 cm, e.g. about 3.5 cm, e.g. about 6.5 cm. Spike 20 may have a diameter slightly larger than the diameter of the hole of laminated packaging system 4, e.g. a diameter of a few mm, e.g. between 0.2 and 0.8. mm, e.g. about 0.4 mm, larger than the diameter of the hole of laminated packaging system 4. Spike 20 may have a diameter of about 0.3 cm to about 3 cm, e.g. of about 0.4 cm to about 3.2 cm, e.g. of about 0.6 cm to about 2.4 cm, e.g. of about 1.4 cm to about 1.7 cm or about 1.5 cm to about 1.6 cm, preferably about 0.6 cm, e.g. about 0.64 cm.

Fluid passageway 5a of spike 20 may be of the same length or of shorter length compared to air passageway 7a. It may be of shorter length than air passageway 7a. Fluid passageway may be of a length of about 0.5 to about 5 cm, e.g. about 0.5 to about 3 cm, e.g. about 1 cm, e.g. to permit complete emptying of laminated paper packaging system, e.g. when placed in an inverted orientation. The diameter of fluid passageway 5a may be up to about 15 mm, e.g. up to about 6 mm, e.g. 6.4 mm, more preferably between about 3 and about 15 mm, e.g. between about 6 and about 15 mm, e.g. between about 13 and 14 mm, e.g. about 13.5 mm.

In one embodiment of the invention, fluid passageway 5a of spike 20 may be offset from the center, e.g. center axis, thereof.

Figure 8:
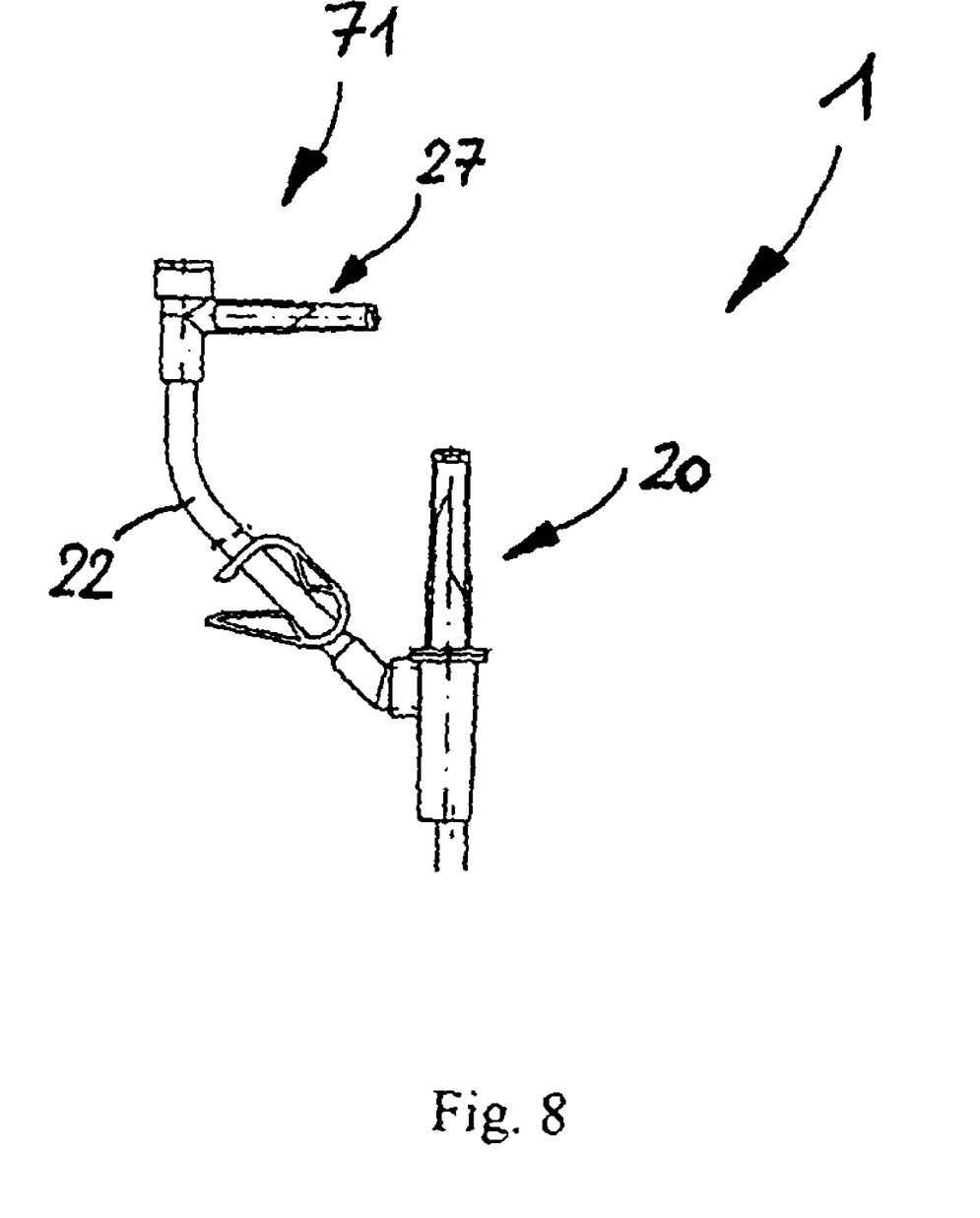
FIG. 8 shows still a further embodiment of a connector device-according to the invention and FIGS. 9A-9F show various embodiments of prefabricated enteral administration systems according to the invention, the systems already being provided with a connector device.

FIG. 8 shows a further embodiment of the connector device 1 of the invention, which is somehow a combination of the embodiments shown in FIG. 6 and FIG. 7. As shown in FIG. 8, connector device 1 comprises a spike 20 and a visualization tube 22. One end of visualization tube 22 is connected the passageway for the composition, and the other end of visualization tube 22 is connected to a venting means 71. Venting means 7 comprises spike 27 for penetration at a predetermined level into the interior of laminated paper packaging system 4 (not shown in FIG. 8), however, spike 20 extends in the transverse direction so as to penetrate into the interior of laminated paper packaging system through the side wall.

The advantage of the embodiments shown in FIG. 6 and FIG. 8 is, that the level of composition in the laminated paper packaging system is visible while the laminated paper packaging system need not be changed at all, since the "level indicator" is an external part, i.e. a part of connector device 1 to be attached to the laminated paper packaging system independent from its shape.

The connector devices already discussed may comprise a tamper-proof system adapted to indicate that the laminated paper packaging system has been connected to the connector device and/or has opened the laminated paper packaging system. Such a tamper-proof system may comprise an indicator member that can for example be associated with section 6 (see FIG. 2) of the connector device by one or more breakable connections, e.g. by means of bridges. These connections may be broken when the connector device is connected to the laminated paper packaging system, for example to the frame-like member 11 thereof. Such tamper-proof systems are known to one skilled in the art, and are described e.g. in U.S. Pat. No. 6,223,924 or EP0947433, which are hereby incorporated by reference.

Tamper-proof system may comprise means provided in connector device, e.g. in tubular member associated with connector device 1, such means being adapted to move unidirectionally over laminated paper packaging system 4, e.g. over frame-like member 11. Such means may comprise indentations, e.g. indentations configured in a saw-tooth manner adapted to move unidirectionally over e.g. a ratchet pawl provided in frame-like member 11, thereby preventing removal of connector device 1 from laminated paper packaging system 4 (not shown). Such means are known to one skilled in the art and are described e.g. in EP0947433, which is hereby incorporated by reference.

The connector devices described above may be made from a plastic or polymeric material, including but not limited to polyolefin, e.g. polypropylene or polyethylene. The connector devices may in particular be made from a material that has low permeability to oxygen. They may be opaque or substantially transparent, or may comprise a portion which is substantially transparent, e.g. section 5 adapted to be connected to the feeding line of the enteral administration set. As already mentioned, the connector devices may be manufactured by molding technology, e.g. by injection molding.

A cap or a seal may be placed over the external ends of the connector device 1 in order to prevent contamination of the connector device 1 before use. For example, a cap may be threaded, e.g. screw threaded, to section 5 (see FIG. 2) of the connector device and/or to section 6 of the connector device. Such a cap may be removed before connecting connector device 1 to the feeding line and/or to the laminated paper packaging system.

A further aspect of the invention deals with a prefabricated enteral administration system comprising one of the embodiments of the connector devices 1 as described above and an enteral administration set 3. The connector device 1 is non-releasably connected to the enteral administration set, in particular to feeding line 2 of enteral administration set 3. The non-releasable connection of connector device 1 to feeding line 2 may for example, be manufactured by methods including but not limited to application of hot melt adhesive, e.g. glue, heat induction, ultrasonic welding and friction welding or any other suitable methods known in the art. The connector device 1 may be molded to the feeding line to form one single unit. The material of the connector device 1 may be capable of forming a seal, e.g. airtight and/or liquid-tight seal, with the material from which the feeding line of the enteral administration set is made. Preferably, the prefabricated enteral administration system is a single-use, i.e. a disposable system, that is disposed of after one single use, so as to reduce the risk of a non-complete sterilization.

Figures 9A, 9B:
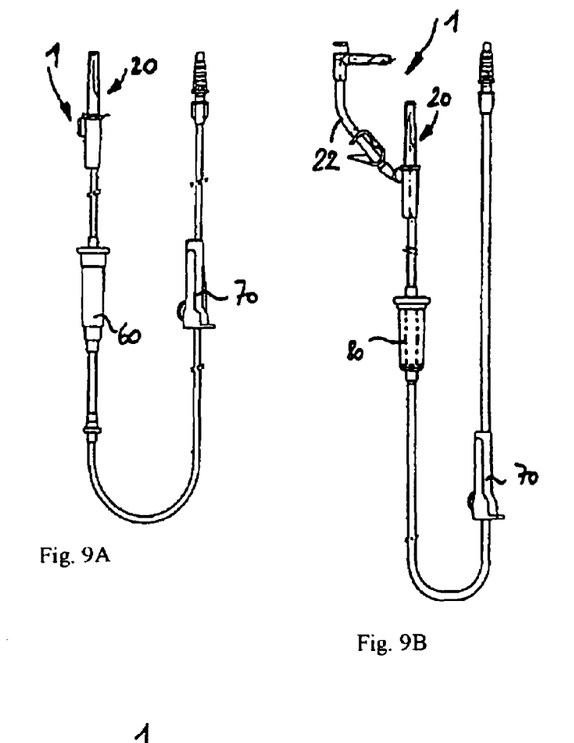
Figure 9C:
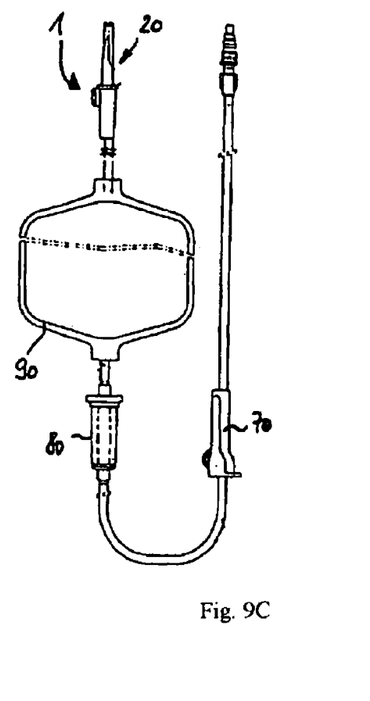

FIGS. 9A-9F show various embodiments of such a prefabricated enteral administration system. Generally, the three embodiments shown in FIGS. 9A, 9B, and 9C are provided with a connector device 1 having a spike 20 (see FIG. 7) for penetration into the interior of laminated paper packaging system 4 (not shown), while those embodiments shown in FIGS. 9D, 9E, and 9F comprise a connector device 1 intended to be screwed onto the laminated paper packaging system (see FIG. 3), or a frame-like member 11 (not shown) thereof respectively. In addition, the embodiments shown comprise a roller clamp 70 for controlling the speed of administration of composition to the patient.

Figure 9D:
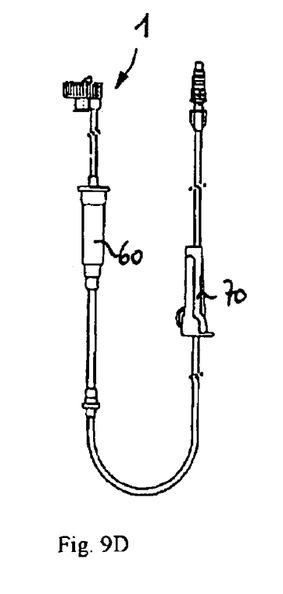
Figures 9E, 9F:
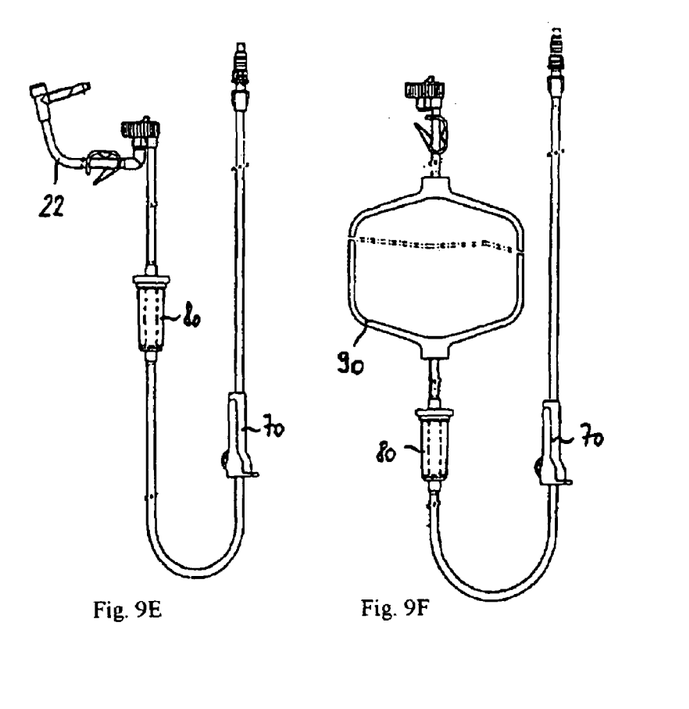

The embodiments shown in FIGS. 9A and 9D further comprise a pumping unit 60 arranged in the feeding line 2 of the enteral administration system for pumping of the composition. The embodiments in FIGS. 9B and 9E are provided with a visualization tube 22 (see FIG. 8) and a venting means comprising an additional spike 7. In addition, the embodiments shown in FIGS. 9B and 9E are provided with a drip chamber 80 for visualization of the flow. Finally, the embodiments shown in FIGS. 9C and 9F are provided with an intermediate transparent bag 90 for accommodating the volume of composition contained in the laminated paper packaging system, so that the composition contained in the laminated paper packaging system may first be emptied out into intermediate transparent bag 90, so that the patient can view the emptying progress. Also, the drip chamber 80 is provided for visualizing the flow of composition.

According to the invention, venting means 7 are optional, particularly when connector device 1 is connected to an enteral set which comprises a pumping unit, or when prefabricated enteral administration systems as hereinabove described comprise a pumping unit.

As already discussed before, such prefabricated enteral administration systems further reduce the risk of contamination and further simplify the handling process.

According to the invention, connector device 1 and prefabricated enteral administration systems as hereinabove described may be sterilisable, e.g. retortable or sterilisable by ethyleneoxide (ETO), gamma-radiation, beta-radiation, peroxide or any other suitable agent, e.g. chemical agent, known to one skilled in the art.

Still a further aspect of the invention deals with an enteral administration kit comprising an enteral administration set, a connector device as described hereinbefore, and a laminated paper packaging system containing a composition to be enterally administered to a patient. Such a kit of parts is advantageous since the patient need not control any inventory, since the kit always comprises all parts necessary for administration. In case the parts are manufactured for single use, they also further reduce the risk of non-complete sterilization.

Still a further aspect of the invention deals with an enteral administration kit comprising a prefabricated enteral administration system as described hereinbefore, and a laminated paper packaging system containing a composition to be enterally administered to a patient. The advantages are essentially the same as those mentioned in the preceding paragraph. In addition, the handling is easier for the patient, since the connector device and the enteral administration set need not be assembled, but are already prefabricated to form a unitary system to be attached to the laminated paper packaging system, thus also reducing the contamination risk.

The connector devices and the prefabricated enteral administration systems as described hereinbefore may be non-releasably connected to the laminated paper packaging system. The irreversible connection of the connector device or prefabricated enteral administration systems to the laminated paper packaging system may involve locking means provided in the connector devices, e.g. in the tubular member associated with the connector device, e.g. as described in EP0947433, which is hereby incorporated by reference.

The present invention provides a use of a laminated paper packaging system in enteral tube feeding, which use comprises directly connecting, e.g. sealably connecting, a laminated paper packaging system to an enteral administration set through the connector devices or to the prefabricated enteral administration systems as hereinabove described.

According to the invention there is further provided a method of enterally administering to a patient in need thereof a medical or nutritional composition contained in a laminated paper packaging system, which method comprises sealably connecting the feeding line of an enteral administration set to the laminated paper packaging system through a connector device as hereinabove described, or the laminated paper packaging system directly to a prefabricated enteral administration systems as described herein, e.g. using a gravity set with roller clamp or a pump set. Such sets are known to one skilled in the art.

In a further aspect there is provided a method for releasably connecting the connector device or the prefabricated enteral administration systems as described herein to a laminated paper packaging system, which method comprises
  (a) removing a seal or cap, e.g. a pull tab, from the laminated paper packaging system, and
  (b) simultaneously opening the laminated paper packaging system, when the connector device or the prefabricated enteral administration system is releasably connected, thereto, and optionally
  (c) connecting a visualization tube 22 to the connector device or the prefabricated enteral administration system and to the laminated paper packaging system.

The invention claimed is:

1. A connector device for connecting a feeding line of an enteral administration set to a laminated paper packaging system containing a composition, the connector device comprising:
  a rigid tube part being adapted to sealingly attach to the feeding line of the enteral administration set, the tube part defining a first part of a passageway allowing the flow of the composition contained in the laminated paper packaging system to the feeding line of the enteral administration set, the tube part comprising a first venting means for venting an interior of the laminated paper packaging system,
  first means for threadably attaching the rigid tube part to the laminated paper packaging system, whereby the connector is screwed to the laminated paper packaging system, the first means further defining a second part of the passageway when threadably attached to the laminated paper packaging system,
  a cutting member for opening the laminated paper packaging system upon screwing the connector device onto the laminated paper packaging system, the cutting member protrudes from an interior of the first means and comprises a center axis that is offset from a center axis of the connector device, and
  third means for fixedly attaching the rigid tube part to the laminated paper packaging system, whereby the connector device is secured to an interior surface within the laminated paper packaging system.

2. A connector device according to claim 1, wherein the laminated paper packaging system includes a first surface with a frame-like member defining an annular threaded projection, and wherein the first means comprises a threaded annular portion complementary to the threaded projection of the laminated paper packaging system.

3. A connector device according to claim 2, wherein the cutting member protrudes from the connector device in a direction towards the laminated paper packaging system for cutting the laminated paper packaging system upon screwing the connector device onto the laminated paper packaging system.

4. A prefabricated enteral administration system comprising an enteral administration set and a connector device non-releasably connected to the enteral administration set, wherein the connector device is a connector device as claimed in claim 1.

5. A prefabricated enteral administration system according to claim 4, further comprising a pump unit arranged in the feeding line of the enteral administration set.

6. A prefabricated enteral administration set according to claim 4, further comprising a transparent intermediate bag for accommodating the volume of composition contained in the laminated paper packaging system.

7. A prefabricated enteral administration system according to claim 4, further comprising a dosing means for controlling the speed of administration of the composition to the patient.

8. An enteral administration kit comprising a prefabricated enteral administration system according to claim 4, and a laminated paper packaging system containing a composition to be enterally administered to a patient.

9. An enteral administration kit comprising an enteral administration set, a connector device according to claim 1, and a laminated paper packaging system containing a composition to be enterally administered to a patient.

10. A connector device for connecting a feeding line of an enteral administration set to a laminated paper packaging system containing a composition and having a first surface, the connector device comprising:
  a rigid tube part being adapted to sealingly attach to the feeding line of the enteral administration set, the tube part defining a first part of a passageway allowing the flow of the composition contained in the laminated paper packaging system to the feeding line of the enteral administration set, the tube part comprising a first venting means for venting an interior of the laminated paper packaging system,
  a tubular first spike for penetrating the first surface of the laminated paper packaging system and defining a second part of the passageway, the first spike defining a point,
  a first rim for fixedly attaching the connector device to the first surface of the laminated paper packaging system upon penetration of the first spike and pressing of the connector device against the first surface of the laminated paper packaging system, the first rim formed of a rigid material and integrally with the connector device, the first rim located at a fixed first distance from the point of the first spike, and a second rim for fixedly attaching the connector device to an interior surface within said laminated paper packaging system, the second rim formed of a flexible material and integrally with the connector device, the second rim located at a fixed second distance from the point of the spike, the second distance being less than the first distance.

11. A connector device according to claim 10, wherein the first venting means comprises a valve means allowing air to enter through the valve means while preventing the composition to be administered to exit.

12. A connector device according to claim 10, further comprising a visualization tube, one end of the visualization tube being connected to the passageway for the composition to be administered and the other end of the visualization tube being connected to a second venting means, the second venting means comprising an of inlet and a second spike adapted to penetrate a second surface of the laminated paper packaging system corresponding to a predetermined fluid level of the composition.

13. A prefabricated enteral administration system comprising an enteral administration set and a connector device non-releasably connected to the enteral administration set, wherein the connector device is a connector device as claimed in claim 10.

14. A connector device according to claim 10, wherein the attachment means comprises an adhesive layer adapted to engage the first surface of the laminated paper packaging system subsequent to penetration of the first spike.

15. A connector device according to claim 14, wherein the attachment means includes a first annular rim on the spike having a surface facing towards the first surface of the laminated paper packaging system during penetration of the first spike, and wherein the adhesive layer is applied to the surface of the first rim.

16. A connector device for connecting an end of a feeding line of an enteral administration set to a laminated paper packaging system containing a composition to be administered through the set, wherein the packaging system includes a surface and a tubular frame-like member projecting from the surface, the frame-like member defining a first threaded portion, the connector device comprising:
  a rigid tithe part adapted to sealingly engage an end of the feeding line, the tube part defining a first part of a passageway for the composition from the laminated paper packaging system to the feeding line;
  first means for threadably attaching the rigid tube part to the laminated paper packaging system, wherein the first means defines a second part of the passageway when threadably attached to the laminated paper packing system, wherein said first means also fixedly attaches the rigid tube part to an interior surface of the laminated paper packaging system; and
  a cutting member rotatable with the connector device upon screwing the connector device onto the frame-like member of the packaging system, the cutting member projecting, toward the surface such that the cutting member first cuts the surface only after engagement of the first means of the connector device with the first threaded portion of the packaging system, the cutting member is integrally formed with first means, protrudes from an interior of the first means and comprises a center axis that is offset from a center axis of the connector device.

17. A prefabricated enteral administration system comprising an enteral administration set and a connector device non-releasably connected to the enteral administration set, wherein the connector device is a connector device as claimed in claim 16.

18. An enteral administration kit comprising a prefabricated enteral administration system according to claim 17, and a laminated paper packaging system containing a composition to be enterally administered to a patient.

19. A connector device according to claim 16, wherein the first means includes a second threaded portion defined on the connector device, the second threaded portion being complementary to the first threaded portion of the frame-like member of the laminated paper packaging system such that the connector device threadably engages the frame-like member of the laminated paper packaging system.

20. A connector device comprising:
  a rigid tube part, a first end sealingly attachable to a feeding line, and a second end sealingly attachable to a package,
  said rigid tube part having formed integrally therewith at about said second end a first rim means comprising a rigid material and a second rim means comprising a flexible material inure distal thereon, the first rim means being located at a fixed distance from the second rim means,
  said rigid tube part having at said second end a spike,
  wherein, upon engagement of said connector device to a top portion of said package, said spike penetrates said top portion of said package, and
  wherein, upon engagement of said connector device to said top portion of said package, said first rim means engages the outer surface of said top portion of said package and said second rim means engages a corresponding inner surface of said top portion of said package, sealingly attaching said connector device to said package between said first and second rim means,
  wherein said second rim means is a thickened portion having a length corresponding to at least a thickness of the package and being located on said rigid tube part, said connector device sealingly engaging the inner surface of said top portion of said package along said thickened portion upon engagement of said connector device to said package.

* * * * *